United States Patent [19]
Helfet

[11] 4,241,730
[45] Dec. 30, 1980

[54] KNEE SUPPORT

[76] Inventor: Arthur J. Helfet, 420 Montebello, Montrose St., 7700 Newlands, Cape Town, South Africa

[21] Appl. No.: 831,187

[22] Filed: Sep. 7, 1977

[30] Foreign Application Priority Data

Sep. 20, 1976 [GB] United Kingdom ............... 38813/76

[51] Int. Cl.³ .............................................. A61F 3/00
[52] U.S. Cl. .................................................. 128/80 C
[58] Field of Search ................. 128/80 C, 80 F, 80 R, 128/87 R, 83; 3/22

[56] References Cited

U.S. PATENT DOCUMENTS

| | | | |
|---|---|---|---|
| 2,654,365 | 10/1953 | Whitaker | 128/80 F |
| 2,877,033 | 3/1959 | Koetke | 128/80 F X |
| 2,883,982 | 4/1959 | Rainey | 128/80 F |
| 3,669,105 | 6/1972 | Castiglia | 128/80 C |
| 3,779,654 | 12/1973 | Horne | 128/80 C |
| 3,801,990 | 4/1974 | Helfet | 128/80 C UX |
| 3,817,244 | 6/1974 | Taylor | 128/80 C |
| 3,902,482 | 9/1975 | Taylor | 128/80 F |

Primary Examiner—John D. Yasko
Attorney, Agent, or Firm—McAulay, Fields, Fisher & Goldstein

[57] ABSTRACT

A knee support is provided for opposing excessive or abnormal strain or torque on the joint. The support has a pair of pivotally interconnected rigid braces one of which snugly embraces the front of the thigh just above the patella and the other of which snugly embraces the front of the shin just below the patella. The pivots are aligned approximately on the mean medial-lateral axis of flexion of the knee and at least the pivot on the lateral side has freedom of universal pivotal motion while that on the medial side has limited freedom of relative bodily displacement in the anterior-posterior direction. Both freedoms are of sufficient magnitude to accommodate the wearer's normal degree of tibial rotation during flexion and extension. Means are provided for locating each brace firmly on its respective component of the limb.

13 Claims, 9 Drawing Figures

KNEE SUPPORT

This invention relates to knee supports for the natural human knee and aims at providing a construction which will resist excessive or abnormal torsional strain on the knee joints such as can occur, for example, when a person stumbles or endeavours to turn too sharply, especially if the whole or the greater part of the body weight is being supported at that instant on one leg.

During normal flexion and extension of a healthy knee, various relative motions occur between the femur and the tibia. The most obvious of these is the large "hinge" motion which normally extends to about 120°. Superimposed on the hinge motion, however, are other and smaller relative motions one of which is termed variously "tibial rotation" and "screw-home". The tibia rotates about its axis relative to the femur by an average of 13°–15°, causing an outward deflection of the foot during extension and inward deflection during flexion. Tibial rotation thus occurs over the range of flexion and extension of the knee which takes place during normal walking and running, and any impediment thereto, or excess torque, due to external forces—such as regularly arise in the course of sports and games by the need for quick and vigorous stopping, starting and turning—can cause internal injury to and derangement of the knee, especially meniscal tearing. A sudden blow or excess force sideways on the knee can also cause tearing of the ligaments.

Ideally, prevention of internal derangement of the knee resulting from any of the above-mentioned external forces would involve some synchronously acting mechanism directly linking the femur and the tibia, but as this would involve the opening of the knee joint by surgery and the implantation of some mechanical device, it represents, for practical purposes, an unrealistic and ideal solution of the problem of knee strain. The present invention therefore aims at providing an approximation to the rigorous but unattainable solution of internal knee derangement as a result of violent or excessive torsional or sideways strain—particularly (but not exclusively) for athletes—by means of an externally applied device which conforms to the normal biological mechanism of the knee joint but resists any abnormal pattern of movement imposed by external force, thereby tending to reduce the risk of damage to the internal structure of the joint.

According to the present invention there is provided a knee support for opposing excessive or abnormal strain on the joint, comprising a pair of pivotally interconnected rigid braces, the one adapted to embrace snugly the front of the thigh just above the patella and the other adapted to embrace snugly the front of the shin just below the patella, the pivots being aligned approximately on the mean medial-lateral axis of flexion of the knee and at least the pivot on the lateral side having freedom of universal pivotal motion whilst that on the medial side has limited freedom of relative bodily displacement in the anterior-posterior direction, both freedoms being of sufficient magnitude to accommodate the wearer's normal degree of tibial rotation during flexion and extension, and means for locating each brace firmly on its respective component of the limb.

Preferably, the lateral pivot is of the ball-and-socket type, and the medial pivot may be of a pin-and-slot or a rack-and-pinion type.

Conveniently, each brace is firmly located on its respective component of the limb by a strap or like binding passing completely round the limb component.

The dimension of the braces, and the extent of the free travel of the medial pivot may need to be tailored to the physical proportions of the wearer's limb. It may also be desirable to make provision for a certain degree of universal motion in the medial pivot as well as that provided in the lateral pivot. The extent of free motion in the medial pivot is mainly dependent on the degree of normal tibial rotation of the wearer's knee, and provision may be required for adjustment of this, for example by means of an adjustable stop at one end of the slot. Furthermore, since it is essential that the support as a whole should impose no restraint on the natural tibial rotation of the knee but maximum restraint on both excessive or insufficient rotation due to external forces, it may be advantageous to form the medial pivot as a rack-and-pinion type articulation so as to dictate the relative displacement of the braces about the universal-motion lateral pivot. A convenient equivalent to a rack and pinion is a taut inelastic cord anchored at its free ends to the ends of the slot and wrapped round the pin in non-slip manner.

Two practical embodiments of the present invention will now be described, by way of illustration only, with reference to the accompanying drawings in which.

Figure 1:
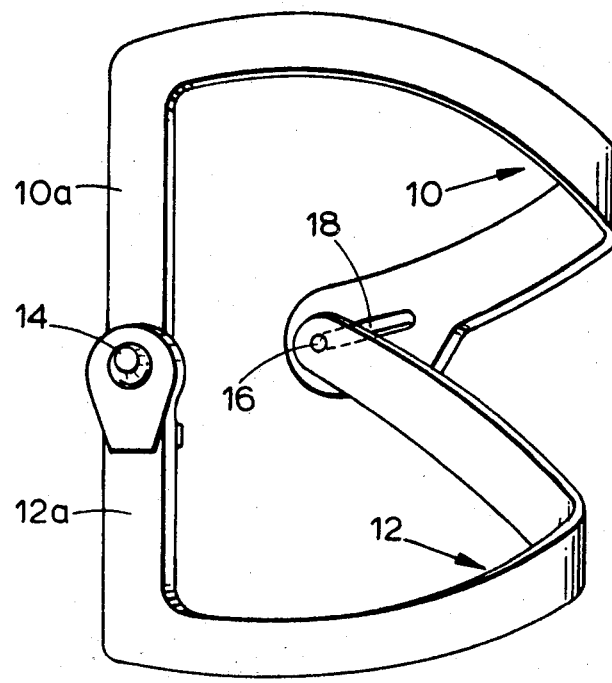
FIG. 1 is an elevation, seen from the lateral side, of a first embodiment of knee support, comprising a pair of pivotally interconnected braces for a right knee in their relative positions at full extension.

The knee support illustrated in FIGS. 1 to 5 consists basically of two generally C-shaped rigid braces 10, 12. These are preferably of a high grade light alloy which may be coated with a plastics layer, at least on its internal surface, to improve wearer comfort. On the lateral side each brace is bent at right-angles into a straight extension 10a, 12a respectively which is adapted to lie close to the wearer's leg. The free ends of these straight lateral extensions are articulated together by a ball-and-socket joint 14 which has freedom of normal pivotal motion for at least 120° and freedom of universal motion over a cone angle of several degrees to the common plane containing the extensions 10a, 12a.

The other, curved, ends of the braces 10, 12 are articulated together by a pin-and-slot connection 16, 18. In this articulation also the pin 16, preferably has a limited freedom of universal motion—mainly to avoid jamming because of the mutual changes of plane of the two ends of the braces during flexion and extension of the knee. The pin 16 itself, however, is a relatively close fit diametrically within the slot 18.

Figure 8:
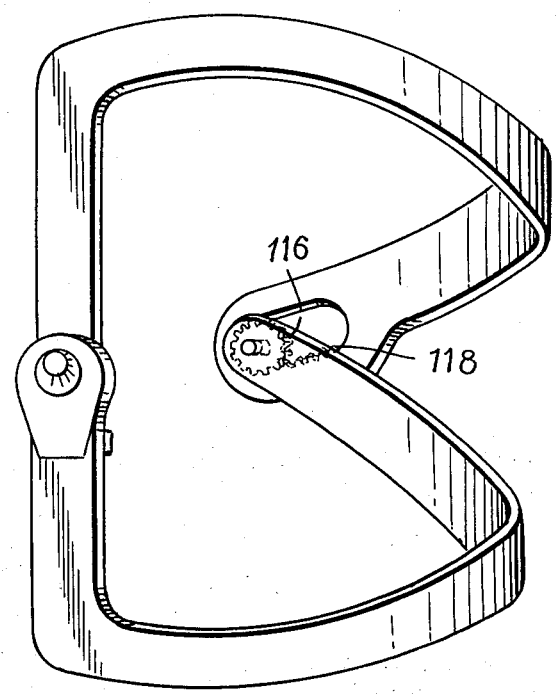
FIG. 8 is an elevation, seen from the lateral side, of a third embodiment of knee support.
Figure 9:
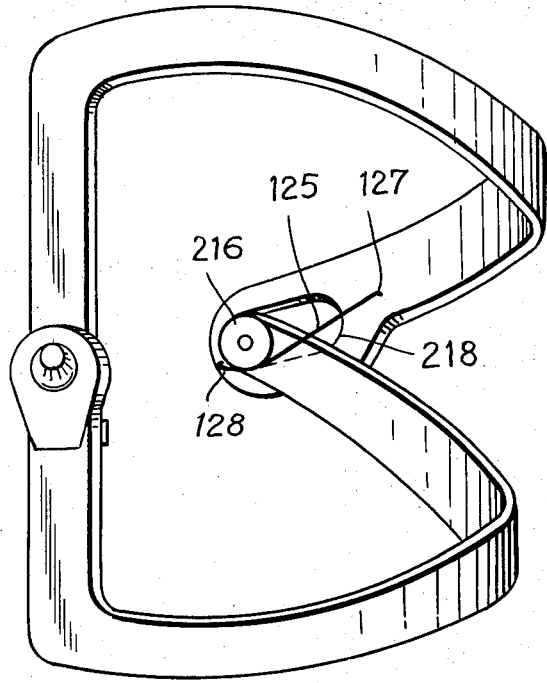
FIG. 9 is a similar view of a fourth embodiment.

As has already been suggested in British Pat. No. 1,377,561, which related to knee joints for artificial limbs, it may be found desirable to form the pin and slot articulation 16, 18 in the manner of a rack and pinion, as shown in FIG. 8. The pinion 116 is displaced along the toothed slot or rack 118 synchronously, with the tibial rotation taking place naturally in the knee joint. A further alternative is shown in FIG. 9, where an inelastic cord 125 may be wrapped around, and anchored to, the pin 216 and have its ends 127, 128 anchored to the ends of the slot 218. This is a relatively frictionless non-slip drive mechanism which ensures rolling of the pin 216 without slipping on the appropriate longitudinal wall of the slot 218.

The manner of securing the braces 10, 12 to the wearer's leg is shown as a strong webbing strap or binding 20, 22 respectively. It may also be desirable to shape each brace 10, 12 so as to fit closely the contour of the relative bones where they approach nearest the surface of the skin. The material of the binding 20, 22 may also be locally reinforced or substituted by a piece of specially contoured non-deformable material which fits snugly over or into a portion of the thigh or shin component—for example, a pad which fits snugly into the thigh cavity behind the knee. Such localised formations reduce the risk that either brace, 10, 12 will tend to rotate with the flesh relative to the respective bone and thus become less effective as a restraint on excessive or abnormal torque at the condylar surfaces of the knee joint.

The structure of each brace 10, 12 is optional but lightness and rigidity are the principal requirements, coupled with a comfortable inward surface which makes contact with the wearer's flesh. Similarly, the exact structure of the ball and socket joint 14 and of the pin and slot articulation 16, 18 is optional provided that both articulations acting in concert permit a tibial rotation of approximately 15°.

The braces 10, 12 may sometimes require to be "tailored" to a particular wearer's leg, but it is envisaged that a given size and contour of the brace will suitably fit a significant number of wearers even though they may differ considerably in height, weight and physique. Obviously, however, the optimum results in the task of opposing excessive torque on the knee joint are to be expected from a support whose braces 10, 12 and preferably also their respective anchorages 20, 22 are tailored to the contours and structure of each particular wearer.

Figure 6:
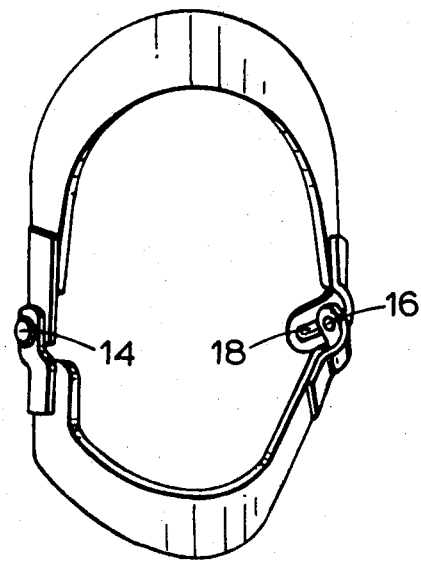
FIG. 6 is a front elevation of a second embodiment of the invention.
Figure 7:
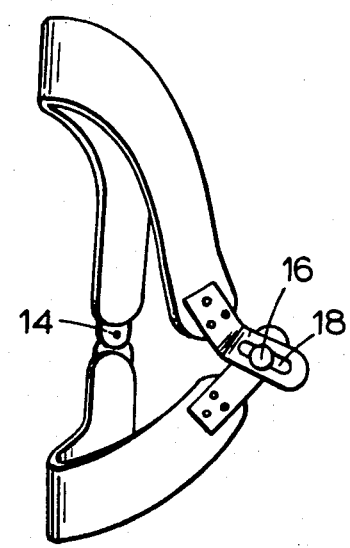
FIG. 7 is a side elevation of the embodiment of FIG. 6.
Figure 2:
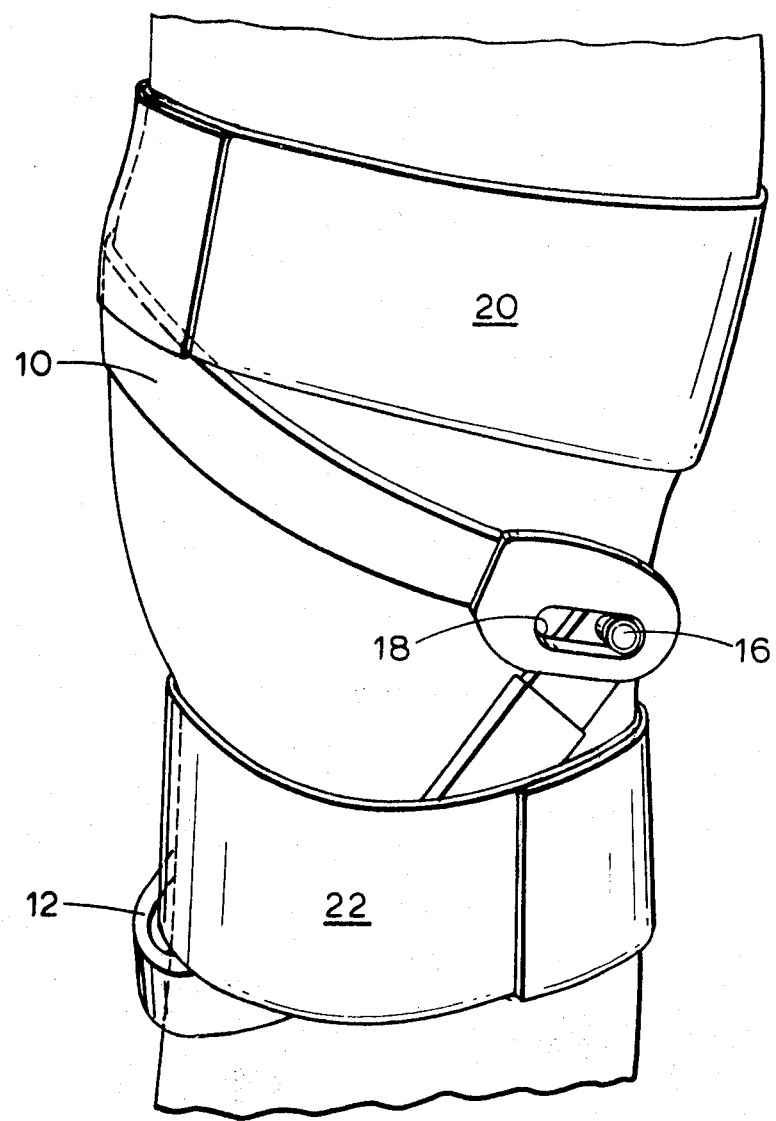
FIG. 2 is an elevation, seen from the medial side, of the braces in position on the right knee when in full extension.
Figure 3:
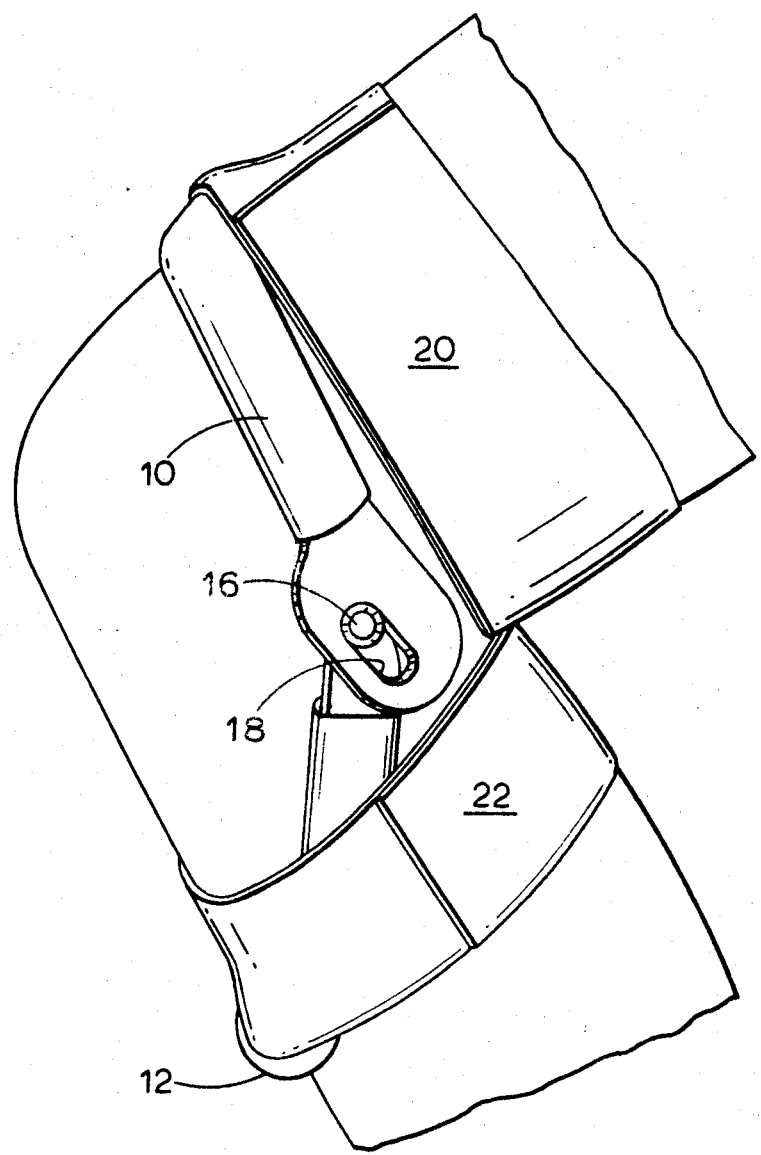
FIG. 3 is a view similar to FIG. 2 showing the knee flexed to approximately 90°.
Figure 4:
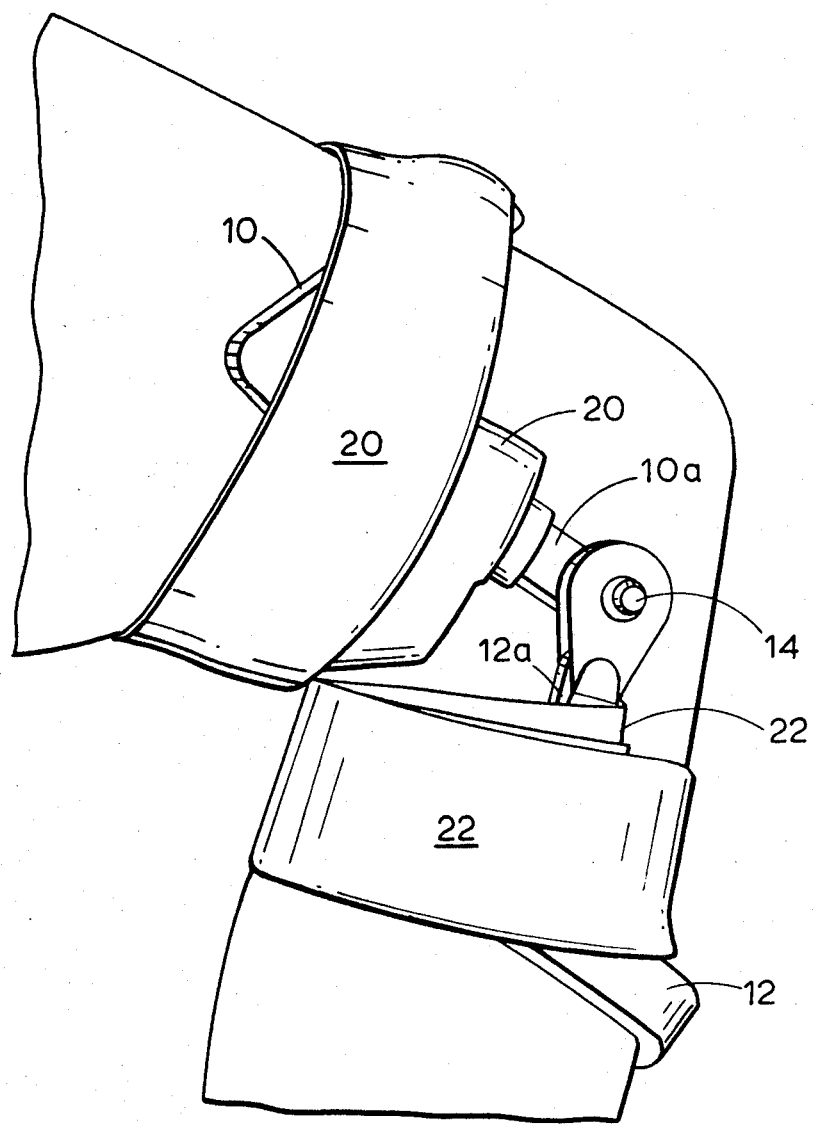
FIG. 4 is a view similar to FIG. 3 but seen from the lateral side.
Figure 5:
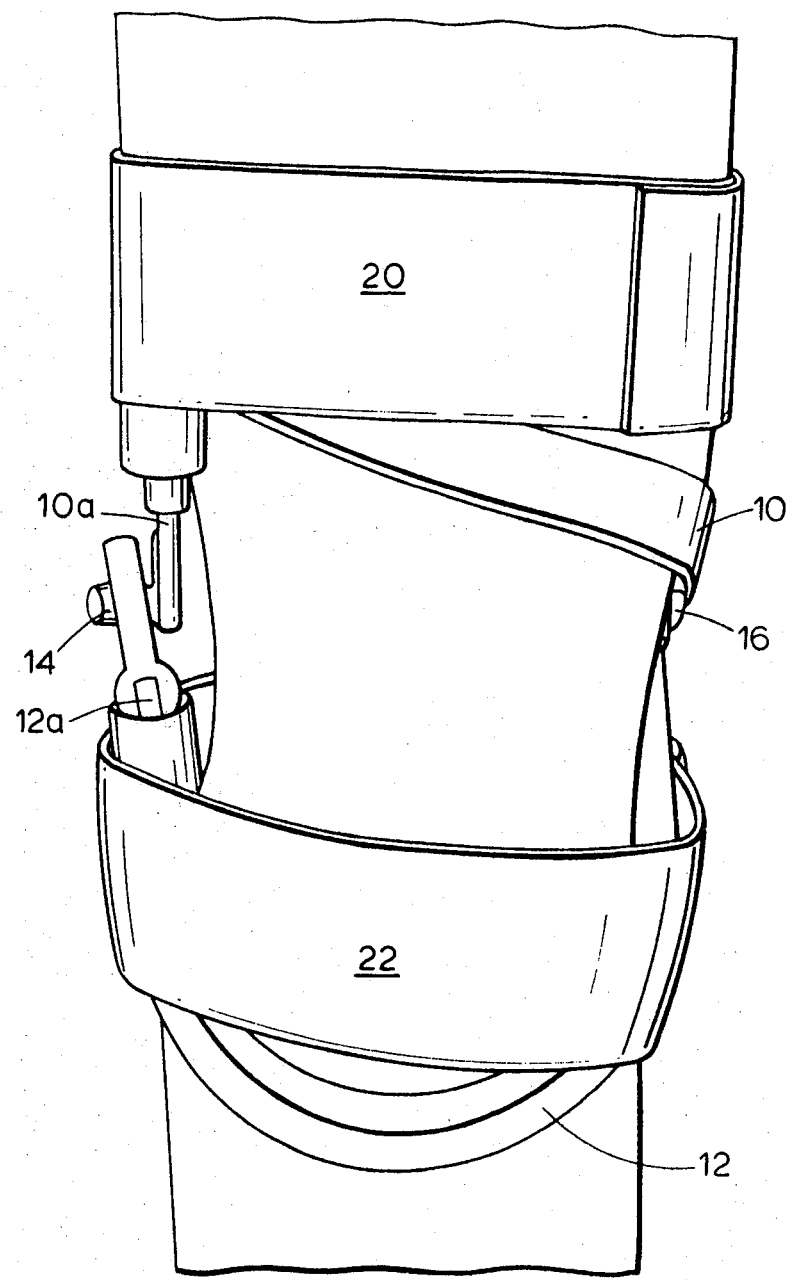
FIG. 5 is an anterior elevation of FIG. 2.

The embodiment illustrated in FIGS. 6 and 7 is similar in operation to that illustrated in FIGS. 1 to 5, and differs in that joint 14 and the pin and slot connection 16, 18 are formed in respective pairs of joint members which are secured to the rest of the brace rather than being integral with it. All of the brace apart from the joint members can be made of a plastics material, and the joint members may be of metal, for example, stainless steel.

I claim:

1. A knee support for opposing excessive or abnormal strain on the joint, comprising a pair of pivotally interconnected rigid braces, the one adapted to embrace snugly the front of the thigh just above the patella and the other adapted to embrace snugly the front of the shin just below the patella, the pivots being aligned approximately on the mean medial-lateral axis of flexion of the knee and at least the pivot on the lateral side having freedom of universal pivotal motion whilst that on the medial side has limited freedom of relative bodily displacement in the anterior-posterior direction, both freedoms being of sufficient magnitude to accommodate the wearer's normal degree of tibial rotation during flexion and extension, and means for locating each brace firmly on its respective component of the limb.

2. A knee support as claimed in claim 1, wherein the lateral pivot is provided by a ball and socket joint.

3. A knee support as claimed in claim 1, wherein the medial pivot is provided by a pin slidably engaging in a slot.

4. A knee support as claimed in claim 3, wherein a taut, inelastic string is secured by its ends to opposite ends of the slot and is wrapped around the anchored to the pin.

5. A knee support as claimed in claim 1, wherein the medial pivot is provided by a rack and pinion joint.

6. A knee support as claimed in claim 1, wherein each brace has a respective joint member secured to each end thereof, the joint members providing the lateral and medial pivots.

7. A knee support for protection of the knee by opposing excessive or abnormal strain on the knee joint during physical activity, the support comprising a pair of rigid braces, the first brace being adapted to embrace snugly the front of the thigh just above the patella and the second brace being adapted to embrace snugly the front of the shin just below the patella, each brace extending approximately from the medial side to the lateral side of the leg portion being embraced; a lateral side pivot means connecting the two braces and adapted to be located approximately on the lateral side of the mean medial-lateral axis of flexion of the knee, the lateral side pivot having freedom of universal pivotal motion; and medial side pivot means connecting the two braces on the medial side and and adapted to be located approximately on the mean medial-lateral axis of flexion of the knee, the medial side pivot having limited freedom of relative bodily displacement in the anterior-posterior direction, both freedoms being of sufficient magnitude to accommodate the wearer's normal degree of tibial rotation during flexion and extension; and securing means for locating and securing each brace firmly on its respective limb component.

8. The knee support of claim 7 wherein the combined action of the medial and lateral joints permit a tibial rotation by the wearer of approximately 15°.

9. An articulated knee support for protection of the knee, by opposing excessive or abnormal strain on the knee joint during physical activity, the support comprising a first brace and a second brace, each brace being generally C-shaped and rigid and adapted to fit against and extend across the front of the leg of the wearer, above and below the patella, respectively; a straight extension, extending at right angles from the lateral end of each brace toward the other brace, adapted to extend adjacent the lateral side of a wearer's leg; a ball-and-socket type universal joint connecting the straight extensions; a second pivoting joint connecting the medial portions of the braces and having the capability of limited relative bodily displacement in the anterior-posterior direction; the two joints being adapted to be located approximately on the medial lateral axis of flexion of the knee, when the two braces are properly fitted against the leg of the wearer; the two pivots being adapted to accommodate the wearer's normal degree of tibial rotation during flexion and extension, and strap means for firmly securing each brace to the proper location on the limb of the wearer.

10. The support of claim 9 wherein the medial pivot comprises a pin-in-slot joint.

11. The support of claim 10 wherein the pin has the capacity of a limited freedom of universal motion.

12. The support of claim 10 wherein the pin and slot pivot joint is formed as a rack and pinion.

13. The support of claim 10 wherein the medial and lateral joints acting in concert permit a tibial rotation of approximately 15°.

* * * * *